(12) United States Patent
Sandham et al.

(10) Patent No.: US 8,431,703 B2
(45) Date of Patent: *Apr. 30, 2013

(54) PYRROLOPYRIDINE COMPOUNDS AND THEIR USE IN TREATING DISEASE

(75) Inventors: David Andrew Sandham, Horsham (GB); Catherine Leblanc, Horsham (GB); Lyndon Nigel Brown, Horsham (GB)

(73) Assignee: Novartis AG, Basel (CH)

( * ) Notice: Subject to any disclaimer, the term of this patent is extended or adjusted under 35 U.S.C. 154(b) by 1009 days.

This patent is subject to a terminal disclaimer.

(21) Appl. No.: 12/096,448

(22) PCT Filed: Dec. 7, 2006

(86) PCT No.: PCT/EP2006/069416
§ 371 (c)(1),
(2), (4) Date: Jun. 6, 2008

(87) PCT Pub. No.: WO2007/065924
PCT Pub. Date: Jun. 14, 2007

(65) Prior Publication Data
US 2008/0287416 A1    Nov. 20, 2008

(30) Foreign Application Priority Data
Dec. 9, 2005   (GB) .................................. 0525143.4

(51) Int. Cl.
*C07D 471/02*        (2006.01)
*A61K 31/44*         (2006.01)

(52) U.S. Cl.
USPC .......................................... 546/113; 514/300

(58) Field of Classification Search .................. 546/113; 514/300
See application file for complete search history.

(56) References Cited

U.S. PATENT DOCUMENTS

| 5,212,195 | A    | 5/1993  | Clark et al.    |         |
|-----------|------|---------|-----------------|---------|
| 6,248,753 | B1   | 6/2001  | Chen            |         |
| 7,662,832 | B2 * | 2/2010  | Kim et al.      | 514/300 |
| 7,666,878 | B2 * | 2/2010  | Bala et al.     | 514/300 |
| 2008/0312229 | A1 | 12/2008 | Sandham et al. |         |
| 2008/0312230 | A1 | 12/2008 | Sandham        |         |
| 2010/0204225 | A1* | 8/2010 | Bala et al.    | 514/234.5 |
| 2010/0210610 | A1* | 8/2010 | Bala et al.    | 514/171 |

FOREIGN PATENT DOCUMENTS

| EP | 1 424 325 A1   | 6/2004  |   |
|----|----------------|---------|---|
| EP | 1 505 061 A1   | 2/2005  |   |
| WO | WO95/07910 A1  | 3/1995  |   |
| WO | WO 95/07910 A1 | 3/1995  |   |
| WO | WO 95/33748 A1 | 12/1995 |   |
| WO | WO 02/34747 A1 | 5/2002  |   |
| WO | WO 03/066047 A1 | 8/2003 |   |
| WO | WO 2004/007451 A1 | 1/2004 |   |
| WO | WO 2004/069782 A2 | 8/2004 |   |
| WO | WO 2005/040112 A1 | 5/2005 |   |
| WO | WO2005/102338 A1 | 11/2005 |   |
| WO | WO 2005/121141 A1 | 12/2005 |   |
| WO | WO2005/123731 A2 | 12/2005 |   |
| WO | WO 2006/025716 | * | 3/2006 |
| WO | WO2006/042102 A2 | 4/2006 |   |

OTHER PUBLICATIONS

Bala, U.S. PTO Office Action, U.S. Appl. No. 12/699,723, Feb. 14, 2012, 18 pgs.
Brodrick et al., "1 H-Pyrrolo[2,3-b]pyridines. Part III. A Novel Synthetic Route From 1-Substituted 2-Aminopyrroles", J. Organic Chemistry, vol. 19 (1975), pp. 1910-1913.
Hodge et al., "Corticotropin-Releasing Hormone Receptor Antagonists: Framework Design and Synthesis Guided by Ligand Conformational Studies", J. Med. Chem., vol. 42 (1999), pp. 819-832.
Mouaddib et al., "Synthesis of Benzo[5'6']cyclohepta[4,5]pyrrolo[2,3-beta]pyridin-12-one", Tetrahedron Letters, vol. 40 (1999), pp. 5853-5854.
Mouaddib et al., "Synthesis of Indolo[3,2-c]quinoline and Pyrido[3',2':4,5][3,2-c]quinoline Derivatives", Synthesis, vol. 4 (2000), pp. 549-556.
Verbiscar, "Synthesis of 1-*p*-Chlorobenzyl-7-azaindole-3-alpha-piperidylmethanol as a Potential Antimalarial Agent", Journal of Medicinal Chemistry, vol. 15, No. 2 (1975), pp. 149-152.
Yakhonotov et al., Biol. Aktivn. Soedin, Akad, Nauk SSSR (1965), pp. 83-90.
Yakhontov et al., Khimiya Geterotsiklicheskikh Soedinenii, vol. 1 (1967), pp. 141-144.

* cited by examiner

*Primary Examiner* — John Mabry
(74) *Attorney, Agent, or Firm* — Mark W. Milstead

(57) ABSTRACT

There are provided according to the invention compounds of formula (I)

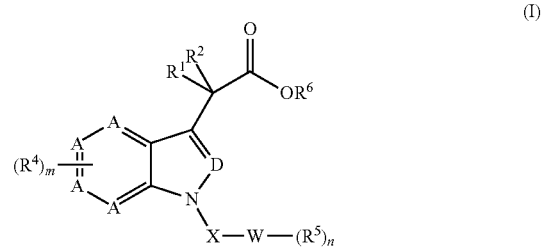

in free ors salt form, wherein
$R^1$, $R^2$, $R^4$, $R^5$, $R^6$, A, D, X, W, m and n are as described in the specification, process for preparing them, and their use as pharmaceuticals.

5 Claims, No Drawings

PYRROLOPYRIDINE COMPOUNDS AND THEIR USE IN TREATING DISEASE

This application is a U.S. National Phase filing of PCT/EP2006/069416 filed 7 Dec. 2006, and claims priority to GB Patent Application 0525143.4 filed 9 Dec. 2005, the contents of which are incorporated herein by reference in their entirety.

The present invention relates to organic compounds, their preparation and their use as pharmaceuticals.

In a first aspect, the present invention provides compounds of formula (I)

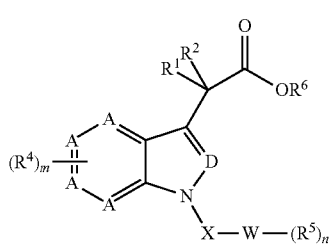

in free or salt form, wherein

A is selected independently from CH and at least one nitrogen;

D is selected independently from $CR^3$ and nitrogen;

$R^1$ and $R^2$ are, independently, H, halogen or $C_1$-$C_8$-alkyl, or $R^1$ and $R^2$ together with the carbon atom to which they are attached, form a $C_3$-$C_{15}$-carbocyclic group;

$R^3$ is selected from $C_1$-$C_8$-alkyl, halogen, cyano, hydroxyl, amino, aminoalkyl, amino(di)alkyl, a $C_3$-$C_{15}$-carbocyclic group, $C_1$-$C_8$-haloalkyl, $C_1$-$C_8$-alkoxy-$C_1$-$C_8$-alkyl, and $C_1$-$C_8$-hydroxyalkyl;

$R^4$ is selected from halogen, $C_1$-$C_8$-alkyl, $C_1$-$C_8$-haloalkyl, a $C_3$-$C_{15}$-carbocyclic group, $C_6$-$C_{15}$-aromatic carbocyclic group, nitro, cyano, $C_1$-$C_8$-alkylsulfonyl, $C_1$-$C_8$-alkylsulfinyl, $C_1$-$C_8$-alkylcarbonyl, $C_1$-$C_8$-alkoxycarbonyl, $C_1$-$C_8$-alkoxy, $C_1$-$C_8$-haloalkoxy, carboxy, carboxy-$C_1$-$C_8$-alkyl, amino, $C_1$-$C_8$-alkylamino, di($C_1$-$C_8$-alkyl)amino, $SO_2NH_2$, ($C_1$-$C_8$-alkylamino)sulfonyl, di($C_1$-$C_8$-alkyl)aminosulfonyl, aminocarbonyl, $C_1$-$C_8$-alkylaminocarbonyl, di($C_1$-$C_8$-alkyl)aminocarbonyl and a 4- to 10-membered heterocyclic group;

$R^5$ is selected from

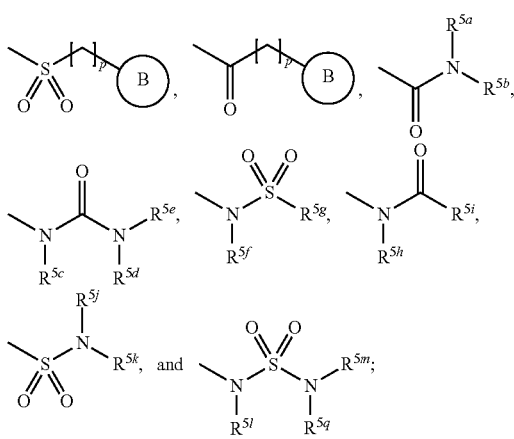

$R^{5a}$ and $R^{5b}$ are independently selected from H, a 4- to 14-membered heterocyclic group, a $C_6$-$C_{15}$-aromatic carbocyclic group, a $C_3$-$C_{15}$-carbocyclic group, and $C_1$-$C_8$-alkyl optionally substituted by 4- to 14-membered heterocyclic group or $C_3$-$C_{15}$-carbocyclic group where at least one of $R^{5a}$ or $R^{5b}$ is $C_1$-$C_8$-alkyl substituted by a 4- to 14-membered heterocyclic group or $C_3$-$C_{15}$-carbocyclic group, or $R^{5a}$ and $R^{5b}$ together with the nitrogen atom to which they are attached form a 4- to 14-membered heterocyclic group, $R^{5c}$, $R^{5d}$ and $R^{5e}$ are independently selected from H, and $C_1$-$C_8$-alkyl optionally substituted by a 4- to 14-membered heterocyclic group, a $C_6$-$C_{15}$-aromatic carbocyclic group, a $C_3$-$C_{15}$-carbocyclic group, or $R^{5c}$ along with $R^{5d}$ or $R^{5e}$ together with the nitrogen atoms to which they are attached and the carbonyl form a 5- to 14-membered heterocyclic group;

$R^{5f}$ is H, $C_1$-$C_8$-alkyl optionally substituted by a 4- to 14-membered heterocyclic group or $C_3$-$C_{15}$-carbocyclic group;

$R^{5g}$ is selected from H, and $C_1$-$C_8$-alkyl optionally substituted by a 4- to 14-membered heterocyclic group or $C_3$-$C_{15}$-carbocyclic group;

$R^{5f}$ and $R^{5g}$ together with the $NSO_2$ group to which they are attached form a 5- to 14-membered heterocyclic group;

$R^{5h}$ and $R^{5i}$ are independently selected from H, and $C_1$-$C_8$-alkyl optionally substituted by a 4- to 14-membered heterocyclic group or $C_3$-$C_{15}$-carbocyclic group, or $R^{5h}$ and $R^{5i}$ together with the NCO group to which they are attached form a 5- to 14-membered heterocycle;

$R^{5j}$ and $R^{5k}$ are independently selected from H, and $C_1$-$C_8$-alkyl optionally substituted by a 4- to 14-membered heterocyclic group or $C_3$-$C_{15}$-carbocyclic group, or $R^{5j}$ and $R^{5k}$ together with the nitrogen atom to which they are attached form a 4- to 14-membered heterocyclic group;

$R^{5l}$, $R^{5m}$ and $R^{5q}$ are independently selected from H, and $C_1$-$C_8$-alkyl optionally substituted by a 4- to 14-membered heterocyclic group or $C_3$-$C_{15}$-carbocyclic group, or $R^{5l}$ along with $R^{5m}$ or $R^{5q}$ together with the nitrogen atoms of the aminosulfonamide to which they are attached form a 5- to 14-membered heterocyclic group;

B is selected from 4- to 14-membered heterocyclic group, a $C_6$-$C_{15}$-aromatic carbocyclic group, and a $C_3$-$C_{15}$-carbocyclic group;

$R^6$ is H or $C_1$-$C_8$-alkyl;

W is a $C_6$-$C_{15}$-aromatic carbocyclic group or a 4- to 14-membered heterocyclic group;

X is —$SO_2$—, —$CH_2$—, —CON(Y)—, —($V_1$)-T-(V)—, a 5- to 14-membered heterocyclic group or a bond;

Y is $C_1$-$C_8$ alkyl optionally substituted by $C_1$-$C_8$ alkyl, halo, oxo, hydroxyl, amino, amino-$C_1$-$C_8$-alkyl, or amino(di-$C_1$-$C_8$-alkyl);

$V_1$ is $C_1$-$C_7$-alkyl optionally substituted by $C_1$-$C_8$ alkyl, halo, oxo, hydroxyl, amino, amino-$C_1$-$C_8$-alkyl, amino(di-$C_1$-$C_8$-alkyl);

V is $C_0$-$C_7$-alkyl optionally substituted by $C_1$-$C_8$ alkyl, halo, oxo, hydroxyl, amino, amino-$C_1$-$C_8$-alkyl, amino(di-$C_1$-$C_8$-alkyl);

T is oxygen or $NR^7$;

$R^7$ is H or $C_1$-$C_8$-alkyl;

wherein each $C_3$-$C_{15}$-carbocyclic group, $C_6$-$C_{15}$-membered aromatic carbocyclic group and each 4- to 14-membered heterocyclic group, unless otherwise specified is independently optionally substituted by one or more groups selected from halo, oxo, hydroxy, cyano, amino, nitro, carboxy, $C_1$-$C_8$-alkyl, halo-$C_1$-$C_8$-alkyl, $C_1$-$C_8$-alkoxy, $C_1$-$C_8$-alkylcarbonyl, $C_1$-$C_8$-alkylsulfonyl, —$SO_2NH_2$, ($C_1$-$C_8$-alkylamino)-sulfonyl, di($C_1$-$C_8$-alkyl)aminosulfonyl, aminocarbonyl, $C_1$-$C_8$-alkylaminocarbonyl and di($C_1$-$C_8$-alkyl)aminocarbonyl, a $C_3$-$C_{15}$-carbocyclic group, a $C_6$-$C_{15}$-membered aromatic carbocyclic group, a 4- to 14-membered heterocyclic group, cyano-$C_1$-$C_8$-alkyl, hydroxy-$C_1$-$C_8$-alkyl, $C_1$-$C_8$-haloalkyl, amino-$C_1$-$C_8$-alkyl, amino(hydroxy) $C_1$-$C_8$-alkyl and $C_1$-$C_8$-alkoxy optionally substituted by aminocarbonyl;

m and n are each, independently, an integer from 0-3; and p is an integer from 0-4.

According to formula (I) the group

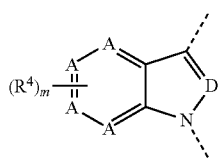

is suitably

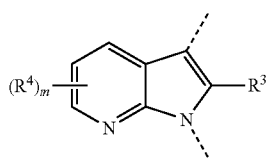

in free or salt form

According to formula (I), $R^1$ and $R^2$ are suitably together H.

According to formula (I), $R^3$ is suitably $C_1$-$C_8$-alkyl, preferably methyl.

According to formula (I), $R^4$ is suitably not present.

According to formula (I), X is preferably —$CH_2$—.

According to formula (I), W is a $C_6$-$C_{15}$ aromatic carbocyclic group, e.g. phenyl. Where W is phenyl, it is suitably 4-substituted by $R^5$.

According to formula (Ia), $R^5$ is suitably

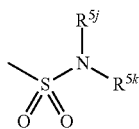

where $R^{5j}$ and $R^{5k}$ together with the nitrogen atom to which they are attached form a 4- to 6-membered heterocyclic group, i.e. piperazine, azetidine, morpholine, piperidine, and pyrrolidine. The 4- to 6-membered heterocyclic group can be optionally substituted by $C_1$-$C_8$-alkyl, preferably methyl, or $R^{5j}$ and $R^{5k}$ are independently selected from $C_1$-$C_8$-alkyl, preferably methyl or a $C_3$-$C_{15}$-carbocyclic group, such as cyclohexane.

According to formula (I), n is 1.

A more preferred embodiment of the present invention provides compounds of formula (Ia)

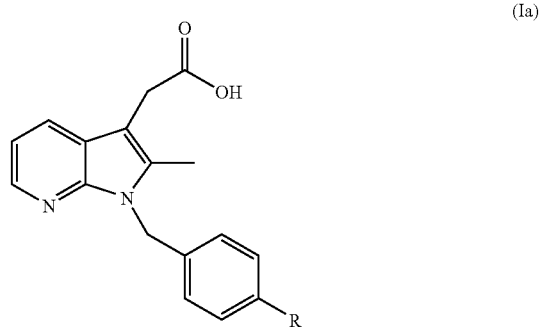

where R is selected from

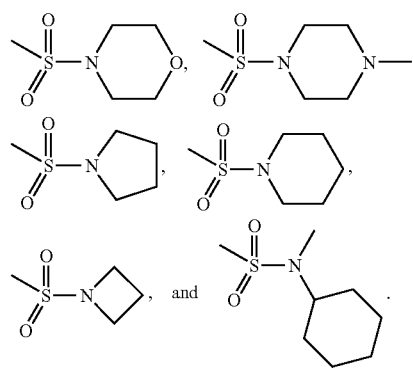

Terms used in the specification have the following meanings:

"Optionally substituted", as used herein, means the group referred to can be substituted at one or more positions by any one or any combination of the radicals listed thereafter.

"Halogen" or "halo" may be fluorine, chlorine, bromine or iodine.

"$C_1$-$C_8$-alkyl" denotes straight-chain or branched $C_1$-$C_8$-alkyl, which may be, e.g., methyl, ethyl, n-propyl, isopropyl, n-butyl, isobutyl, sec-butyl, tert-butyl, straight- or branched-pentyl, straight- or branched-hexyl, straight- or branched-heptyl or straight- or branched-octyl.

"$C_3$-$C_{15}$-carbocyclic group", as used herein, denotes a carbocyclic group having 3- to 15-ring carbon atoms that is saturated or partially saturated, such as a $C_3$-$C_8$-cycloalkyl. Examples of $C_3$-$C_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl, and bicyclodecyl.

"$C_6$-$C_{15}$-aromatic carbocyclic group", as used herein, denotes an aromatic group having 6- to 15-ring carbon atoms. Examples of $C_6$-$C_{15}$-Aromatic carbocyclic groups include but are not limited to phenyl, phenylene, benzenetriyl, naphthyl, naphthylene, naphthalenetriyl or anthrylene.

"$C_1$-$C_8$-alkoxy" denotes straight-chain or branched $C_1$-$C_8$-alkoxy which may be, e.g., methoxy, ethoxy, n-propoxy, isopropoxy, n-butoxy, isobutoxy, sec-butoxy, tert-butoxy, straight- or branched-pentoxy, straight- or branched-hexyloxy, straight- or branched-heptyloxy or straight- or branched-octyloxy. Preferably, $C_1$-$C_8$-alkoxy is $C_1$-$C_4$-alkoxy.

"$C_1$-$C_8$-haloalkyl" and "$C_1$-$C_8$-haloalkoxy" denote $C_1$-$C_8$-alkyl and $C_1$-$C_8$-alkoxy as hereinbefore defined substituted by one or more halogen atoms, preferably one, two or three halogen atoms, preferably fluorine, bromine or chlorine atoms. Preferably, $C_1$-$C_8$-haloalkyl is $C_1$-$C_4$-alkyl substituted by one, two or three fluorine, bromine or chlorine atoms.

"$C_1$-$C_8$-alkylsulfonyl", as used herein, denotes $C_1$-$C_8$-alkyl as hereinbefore defined linked to —$SO_2$—.

"$C_1$-$C_8$-alkylsulfinyl", as used herein, denotes $C_1$-$C_8$-alkyl as hereinbefore defined linked to —SO—.

"Amino-$C_1$-$C_8$-alkyl" and "amino-$C_1$-$C_8$-alkoxy" denote amino attached by a nitrogen atom to $C_1$-$C_8$-alkyl, e.g., $NH_2$—($C_1$-$C_8$)—, or to $C_1$-$C_8$-alkoxy, e.g., $NH_2$—($C_1$-$C_8$)—O—, respectively, as hereinbefore defined.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_8$-alkyl.

"Carboxy-$C_1$-$C_8$-alkyl" and "carboxy-$C_1$-$C_8$-alkoxy" denote carboxy attached by a carbon atom to $C_1$-$C_8$-alkyl or $C_1$-$C_8$-alkoxy, respectively, as hereinbefore defined.

"$C_1$-$C_8$-alkylcarbonyl", "$C_1$-$C_8$-alkoxycarbonyl" and "$C_1$-$C_8$-haloalkylcarbonyl" denote $C_1$-$C_8$-alkyl, $C_1$-$C_8$-alkoxy or $C_1$-$C_8$-haloalkyl, respectively, as hereinbefore defined attached by a carbon atom to a carbonyl group. "$C_1$-$C_8$-alkoxycarbonyl" denotes $C_1$-$C_8$-alkoxy as hereinbefore defined wherein the oxygen of the alkoxy group is attached to the carbonyl carbon.

"$C_1$-$C_8$-alkylamino" and "di($C_1$-$C_8$-alkyl)amino" denote $C_1$-$C_8$-alkyl as hereinbefore defined attached by a carbon atom to an amino group. The $C_1$-$C_8$-alkyl groups in di($C_1$-$C_8$-alkyl)amino may be the same or different.

"$C_1$-$C_8$-alkylaminocarbonyl" and "di($C_1$-$C_8$-alkyl)aminocarbonyl" denote $C_1$-$C_8$-alkylamino and di($C_1$-$C_8$-alkyl)amino, respectively, as hereinbefore defined attached by a nitrogen atom to the carbon atom of a carbonyl group.

"Di($C_1$-$C_8$-alkyl)amino-$C_1$-$C_8$-alkyl" and "di($C_1$-$C_8$-alkyl)amino-$C_1$-$C_8$-alkoxy" denote di($C_1$-$C_8$-alkyl)amino as hereinbefore defined attached by a nitrogen atom to the carbon atom of a $C_1$-$C_8$-alkyl or a $C_1$-$C_8$-alkoxy group, respectively.

"4- to 14-membered heterocyclic group", refers to a 4- to 14-membered heterocyclic ring containing at least one ring heteroatom selected from the group consisting of nitrogen, oxygen and sulphur, which may be saturated, partially saturated or unsaturated (aromatic). Examples of 4- to 14-membered heterocyclic groups include but are not limited to furan, azetidine, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahyrofuran, tetrahydrothiophene, tetrahydrothiopyran, tetrahydropyran, 1,4-dioxane, 1,4-oxathiane, indazole, quinoline, indazole, indole or thiazole. The 4- to 14-membered heterocyclic group can be unsubstituted or substituted. Preferred substituents include halo, cyano, oxo, hydroxy, carboxy, nitro, $C_1$-$C_8$-alkyl, $C_1$-$C_8$-alkylcarbonyl, cyano-$C_1$-$C_8$-alkyl, hydroxy-$C_1$-$C_8$-alkyl, $C_1$-$C_8$-haloalkyl, amino-$C_1$-$C_8$-alkyl, amino(hydroxy)$C_1$-$C_8$-alkyl and $C_1$-$C_8$-alkoxy optionally substituted by aminocarbonyl. Especially preferred substituents include halo, oxo, $C_1$-$C_4$-alkyl, $C_1$-$C_4$-alkylcarbonyl, hydroxy-$C_1$-$C_4$-alkyl, $C_1$-$C_4$-haloalkyl, amino-$C_1$-$C_4$-alkyl and amino(hydroxy)$C_1$-$C_4$-alkyl.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Where in formula (I), m or n are 2, the two substituents may be the same or different. Where m or n are 3, two or all of the substituents may be the same, or all three may be different.

In a yet further aspect, the present invention provides for the use of a compound of formula (I) in any of the aforementioned embodiments, in free or salt form, for the manufacture of a medicament for the treatment of an inflammatory or allergic condition, particularly an inflammatory or obstructive airways disease.

Salts and Isomers

Many of the compounds represented by formula (I) are capable of forming acid addition salts, particularly pharmaceutically acceptable acid addition salts. Pharmaceutically acceptable acid addition salts of the compound of formula (I) include those of inorganic acids, e.g., hydrohalic acids, such as hydrochloric acid or hydrobromic acid; nitric acid; sulphuric acid; phosphoric acid; and organic acids, e.g., aliphatic monocarboxylic acids, such as formic acid, acetic acid, diphenylacetic acid, triphenylacetic acid, caprylic acid, dichloroacetic acid, trifluoroacetic acid, hippuric acid, propionic acid and butyric acid; aliphatic hydroxy acids, such as lactic acid, citric acid, gluconic acid, mandelic acid, tartaric acid or malic acid; dicarboxylic acids, such as adipic acid, aspartic acid, fumaric acid, glutamic acid, maleic acid, malonic acid, sebacic acid or succinic acid; aromatic carboxylic acids, such as benzoic acid, p-chlorobenzoic acid, or nicotinic acid; aromatic hydroxy acids, such as o-hydroxybenzoic acid, p-hydroxybenzoic acid, 1-hydroxy-naphthalene-2-carboxylic acid or 3-hydroxynaphthalene-2-carboxylic acid; and sulfonic acids, such as ethanesulfonic acid, ethane-1,2-disulfonic acid, 2-hydroxyethane-sulfonic acid, methanesulfonic acid, (+)-camphor-10-sulfonic acid, benzenesulfonic acid, naph-thalene-2-sulfonic acid, naphthalene-1,5-disulfonic acid or p-toluenesulfonic acid. These salts may be prepared from compounds of formula (I) by known salt-forming procedures.

Compounds of formula (I) which contain acidic, e.g., carboxyl, groups, are also capable of forming salts with bases, in particular, pharmaceutically acceptable bases, such as those well-known in the art; suitable such salts include metal salts, particularly, alkali metal or alkaline earth metal salts, such as sodium, potassium, magnesium, calcium or zinc salts; or salts with ammonia or pharmaceutically acceptable organic amines or heterocyclic bases, such as benethamine, arginine, benzathine, diethanolamine, ethanolamine, 4(2-hydroxyethyl)morpholine, 1-(2-hydroxyethyl)pyrrolidine, N-methyl glucamine, piperazine, triethanol-amine or tromethamine. These salts may be prepared from compounds of formula (I) by known salt-forming procedures.

In those compounds where there is an asymmetric carbon atom or an axis of chirality the compounds exist in individual optically active isomeric forms or as mixtures thereof, e.g., as racemic or diastereomeric mixtures. The present invention embraces both individual optically active R and S isomers, as well as mixtures, e.g., racemic or diastereomeric mixtures, thereof.

Specific preferred compounds of formula (I) are described hereinafter in the Examples.

The invention also provides a process for the preparation of compounds of formula (I), in free or salt form, which comprises the steps of:

(i) (A) for the preparation of compounds of formula (I), wherein $R^6$ is H, cleaving the ester group —COOR$^6$ in a compound of formula (I),

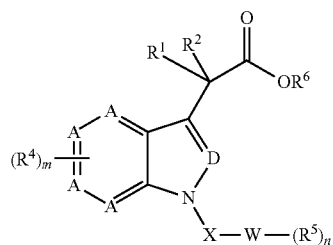

(I)

where $R^6$ is $C_1$-$C_8$-alkyl and $R^1$, $R^2$, $R^4$, $R^5$, A, D, W, X, m, and n are as hereinbefore defined; or (B) for the preparation of compounds of formula (I), wherein $R^6$ is $C_1$-$C_8$-alkyl optionally substituted by $C_3$-$C_{15}$ carbocyclic group, or a $C_3$-$C_{15}$ carbocyclic group, reacting a compound of formula (II)

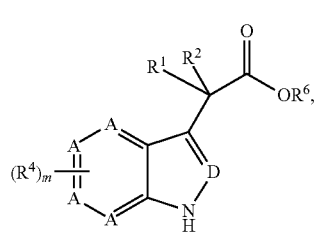

(II)

wherein $R^6$ is $C_1$-$C_8$-alky optionally substituted by $C_3$-$C_{15}$ carbocyclic group, or a $C_3$-$C_{15}$ carbocyclic group I; and $R^1$, $R^2$, $R^4$, A, D and m are as hereinbefore defined with a compound of formula (III)

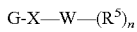 (III)

wherein

G is a leaving moiety, e.g., a halogen atom; and $R^5$, W, X and n are as hereinbefore defined; and (ii) recovering the resultant compound of formula (I) in free or salt form.

Process variant (A) may be carried out using known methods (or analogously as hereinafter described in the Examples) for cleavage of carboxylic ester groups and can be carried out in situ after preparation of a compound of formula (I), where $R^6$ is $C_1$-$C_8$-alkyl optionally substituted by $C_3$-$C_{15}$ carbocyclic group, or a $C_3$-$C_{15}$ carbocyclic group. For example, the compound of formula (I), where $R^6$ is $C_1$-$C_8$-alkyl optionally substituted by $C_3$-$C_{15}$ carbocyclic group, or a $C_3$-$C_{15}$ carbocyclic group, which is conveniently in solution in a polar organic solvent or a mixture thereof with water, may be reacted with an aqueous inorganic base, such as NaOH to hydrolyse the ester group; where the base is NaOH, the reaction may be carried out at a temperature of 10-40° C., conveniently ambient temperature.

Process variant (B) may be carried out using known procedures or analogously as hereinafter described in the Examples. For example, the compound of formula (II) may be reacted with an alkyl halide of formula (III), where G is halogen;

$R^5$, W, X and n are as hereinbefore defined, in the presence of an organic base, such as NaH; the reaction may be carried out in an organic solvent, e.g., a polar aprotic solvent, such as N,N-dimethylformamide (DMF) and may be carried out at 10-40° C., conveniently at ambient temperature Compounds of formula (II) are known or may be obtained by known methods, e.g., as described in U.S. Pat. No. 3,320, 268, or analogously as hereinafter described in the Examples. Compounds of formula (III) are known or may be obtained by known methods, or analogously, as hereinafter described in the Examples.

The compounds of formula (I) in free form may be converted into salt form, and vice versa, in a conventional manner. The compounds in free or salt form can be obtained in the form of hydrates or solvates containing a solvent used for crystallisation. Compounds of formulae (I) and (II) can be recovered from reaction mixtures and purified in a conventional manner. Isomers, such as enantiomers, may be obtained in a conventional manner, e.g., by fractional crystallisation, chiral HPLC resolution or asymmetric synthesis from correspondingly asymmetrically substituted, e.g., optically active, starting materials.

Pharmaceutical Use and Assay

Compounds of formula (I) and (II) and their pharmaceutically acceptable salts, hereinafter referred to alternatively as "agents of the invention", are useful as pharmaceuticals. In particular, the compounds have good CRTh2 receptor modulator activity and may be tested in the following assays.

Filtration Binding Assay Protocol

The binding of CRTh2 modulators is determined using membranes prepared from human CRTh2-expressing Chinese Hamster Ovary cells (CHO.K1-CRTh2). To produce cell membranes CHO.K1-CRTh2 cells cultured in roller bottles are harvested using cell dissociation buffer (Invitrogen). The cells are pelleted by centrifugation (167 g, 5 min). The cell pellet is incubated in hypotonic buffer (15 mM Tris-OH, 2 mM MgCl$_2$, 0.3 mM EDTA, 1 mM EGTA, 1× Complete™ tablet) at 4° C. for 30 min. At 4° C. cells are homogenized using a Polytron® (IKA Ultra Turrax T25) for 5 bursts of 1 second. The homogenate is centrifuged (Beckman Optima™ TL Ultracentrifuge, 48000 g, 30 min at 4° C.). The supernatant is discarded and the membrane pellet resuspended in homogenisation buffer (75 mM Tris-OH, 12.5 mM MgCl2, 0.3 mM EDTA, 1 mM EGTA, 250 mM Sucrose, 1× Complete™ tablet. Membrane preparations are aliquoted and stored at 80° C. The protein content is estimated using Bradford Protein Assay Dye (Bio Rad).

The binding of [$^3$H]-PGD$_2$ (157 Ci/mmol) to CHO.K1-CRTh2 membranes is determined in the absence (total binding) and presence (non-specific binding) of unlabelled PGD$_2$ (1 μM). Subtraction of the cpm (counts per minute) of [$^3$H]-PGD$_2$ binding in presence of excess unlabelled PGD$_2$ from that observed in the absence of excess unlabelled PGD$_2$ is defined as specific binding. Active CRTh2 modulators are able to compete with [$^3$H]-PGD$_2$ for binding to the CRTh2 receptor and are identified in a decrease in the number of cpm bound.

The assay is performed in Greiner U-bottomed 96 well-plates, in a final volume of 100 μl per well. CHO.K1-CRTh2 membranes were diluted in assay buffer (10 mM HEPES-KOH (pH 7.4), 1 mM EDTA and 10 mM MnCl$_2$) and 10 μg are added to each well. [$^3$H]-PGD$_2$ is diluted in assay buffer and added to each well at a final concentration of 2.5 nM. To determine non-specific binding, [$^3$H]-PGD$_2$ binding to the CRTh2 receptor is competed with using unlabelled PGD$_2$ at a final well concentration of 1 μM. The experiment is done in triplicate, with reagents added to the wells as follows:
- 25 μL assay buffer for total binding or
- 25 μL PGD$_2$ to determine non-specific binding
- 25 μL [$^3$H]PGD$_2$
- 50 μL membranes
- 25 μL test compound in DMSO/assay buffer The plates are incubated at room temperature on a shaker for 1 hour, and then harvested (Tomtec Harvester 9600) onto GF/C filter plates using wash buffer (10 mM HEPES-KOH, pH 7.4). The plate is dried for 2 hours, prior to addition of Micro-Scint 20™ (50 μL) and sealing with TopSeal-S™. Plates are then counted using a Packard Top Count instrument, Plates are then read on the Packard Topcount with the 3H Scintillation program (1 min per well).

Ki (dissocation constant for the inhibition) values for the CRTh2 modulators are reported. Ki values are determined using Sigma Plot™ software, using the Cheng-Prussoff equation.

$$Ki = IC_{50}/1 + [S]/Kd$$

where S is the Concentration of Radioligand and Kd is the Dissociation Constant.

CRTH2 cAMP Functional Assay Protocol

This assay is conducted in CHO.K1-CRTh2 cells. cAMP is generated in the cell by stimulating cells with 5 μM forskolin, an adenylate cyclase activator. PGD$_2$ is added to activate the CRTh2 receptor which results in the attenuation of the forskolin-induced cAMP accumulation. Potential CRTh2 antagonists are tested for their ability to inhibit the PGD$_2$-mediated attenuation of the forskolin-induced cAMP accumulation in CHO.K1-CRTh2 cells.

For each concentration value on the dose-response curve, test compounds are prepared in assay stimulation buffer (HBSS, 5 mM HEPES, 10 μM IBMX±0.1% human serum albumin) containing DMSO (3% vol/vol) and 5 μL/well is added to an assay plate (384 well white optiplate).

CHO.K1-CRTh2 cultured in tissue culture flasks are washed with PBS and harvested with dissociation buffer. Cells are washed with PBS and resuspended in stimulation buffer to a concentration of 0.4×10$^6$/mL and added to the assay plate (10 μL/well).

The assay plate is incubated at room temperature on a shaker for 15 minutes.

A mix of agonist (10 nM Prostaglandin D$_2$) and 5 μM forskolin is prepared in assay stimulation buffer and added to the assay plate (5 μL/well).

In addition, a cAMP standard is serially diluted in assay stimulation buffer and added to separate empty wells on the assay plate (20 μL/well). The cAMP standard allows for the quantification of cAMP generated in CHO.K1-CRTH2 cells.

The assay plate is incubated at room temperature on a shaker for 60 minutes.

Cell lysis buffer (Lysis buffer: Milli-Q H$_2$0, 5 mM HEPES, 0.3% Tween-20, 0.1% human serum albumin) is added to a bead mix (containing Alphascreen™ anti-cAMP acceptor beads 0.06 units/IL, Alphascreen™ streptavidin-coated donor beads 0.06 units/μL, biotinylated cAMP 0.06 units/μL, 10 μM IBMX) is prepared under darkened conditions 60 minutes prior to addition to the assay plate. The resulting lysis mix is added to all wells of the assay plate (40 μL/well).

The assay plate is sealed with Topseal-S™ and incubated in the dark at room temperature on a shaker for 45 minutes. The plate is then counted using a Packard Fusion™ instrument.

The resulting counts per minute are converted to nM cAMP by using the prepared cAMP standard curve. IC$_{50}$ values (concentration of CRTh2 antagonist required to inhibit 50% of the PGD$_2$-mediated attenuation of forskolin-induced cAMP accumulation in CHO.K1-CRTh2 cells) are then determined using Prism™ software.

Compounds of the Examples herein below generally have Ki values in the SPA binding assay below 1 μM. For example, the compounds of Examples 1, 2, 4 and 6 have Ki values of 0.030, 0.034, 0.240 and 0.002 μM respectively.

Compounds of the Examples herein below generally have IC$_{50}$ values in the functional assay below 1 μM. For example, the compounds of Examples 1, 2, 4 and 6 have IC$_{50}$ values of 0.060, 0.083, 0.042 and 0.018 μM respectively.

Compounds of formula (I) and (II), in free or salt form, are modulators, of the G-protein-coupled chemoattractant receptor CRTh2, expressed on Th2 cells, eosinophils and basophils. PGD$_2$ is the natural ligand for CRTh2. Thus, modulators which inhibit the binding of CRTh2 and PGD$_2$ are useful in the treatment of allergic and anti-inflammatory conditions. Treatment in accordance with the invention may be symptomatic or prophylactic. "Modulators" as used herein is intended to encompass antagonists, agonists, partial antagonists and/or partial agonists. Preferably, modulators are antagonists. Accordingly, agents of the invention are useful in the treatment of inflammatory or obstructive airways diseases, resulting, e.g., in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitis asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., corticosteroid) or bronchodilatory. Prophylactic benefit in asthma may, in particular, be apparent in subjects prone to "morning dipping". "Morning dipping" is a recognised asthmatic syndrome, common to a substantial percentage of asthmatics and characterised by asthma attack, e.g., between the hours of about 4-6 a.m., i.e., at a time normally substantially distant from any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis including, e.g., aluminosis, anthracosis, asbestosis, chalicosis, ptilosis, siderosis, silicosis, tabacosis and byssinosis.

Having regard to their anti-inflammatory activity, in particular, in relation to inhibition of eosinophil activation, agents of the invention are also useful in the treatment of eosinophil related disorders, e.g., eosinophilia, in particular, eosinophils-related disorders of the airways, e.g., involving morbid eosinophilic infiltration of pulmonary tissues including hypereosinophilia as it effects the airways and/or lungs, as well as, e.g., eosinophil-related disorders of the airways consequential or concomitant to Löffler's syndrome; eosinophilic pneumonia; parasitic, in particular, metazoan, infestation including tropical eosinophilia; bronchopulmonary aspergillosis; polyarteritis nodosa including Churg-Strauss syndrome; eosinophilic granuloma; and eosinophil-related disorders affecting the airways occasioned by drug-reaction.

Agents of the invention are also useful in the treatment of inflammatory or allergic conditions of the skin, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita and other inflammatory or allergic conditions of the skin.

Agents of the invention may also be used for the treatment of other diseases or conditions, in particular, diseases or conditions having an inflammatory component, e.g., treatment of diseases and conditions of the eye, such as conjunctivitis, keratoconjunctivitis sicca and vernal conjunctivitis; diseases affecting the nose including allergic rhinitis; and inflammatory disease, in which autoimmune reactions are implicated or having an autoimmune component or aetiology, including autoimmune hematological disorders, e.g., hemolytic anemia, aplastic anaemia, pure red cell anaemia and idiopathic thrombocytopenia; systemic lupus erythematosus; polychondritis; sclerodoma; Wegener granulamatosis; dermatomyositis; chronic active hepatitis; myasthenia gravis; Steven-Johnson syndrome; idiopathic sprue; autoimmune inflammatory bowel disease, e.g., ulcerative colitis and Crohn's disease; endocrine opthalmopathy; Grave's disease; sarcoidosis; alveolitis; chronic hypersensitivity pneumonitis; multiple sclerosis; primary billiary cirrhosis; uveitis (anterior and posterior); keratoconjunctivitis sicca and vernal keratoconjunctivitis; interstitial lung fibrosis; psoriatic arthritis; and glomerulonephritis, with and without nephrotic syndrome, e.g., including idiopathic nephrotic syndrome or minal change nephropathy.

Other diseases or conditions which may be treated with agents of the invention include septic shock; rheumatoid arthritis; osteoarthritis; proliferative diseases, such as cancer; mastocytosis, atherosclerosis; allograft rejection following transplantation; stroke; obesity; restenosis; diabetes, e.g., diabetes mellitus type I (juvenile diabetes) and diabetes mellitus type II; diarrhoeal diseases; ischemia/reperfusion injuries; retinopathy, such as diabetic retinopathy or hyperbaric oxygen-induced retinopathy; and conditions characterised by elevated intraocular pressure or secretion of ocular aqueous humor, such as glaucoma. Other diseases or conditions which may be treated with agents of the invention include neuropathic pain as described in WO 05/102338.

The effectiveness of an agent of the invention in inhibiting inflammatory conditions, e.g., in inflammatory airways diseases, may be demonstrated in an animal model, e.g., a mouse or rat model, of airways inflammation or other inflammatory conditions, e.g., as described by Szarka et al., *J Immunol Methods*, Vol. 202, pp. 49-57 (1997); Renzi et al., *Am Rev Respir Dis*, Vol. 148, pp. 932-939 (1993); Tsuyuki et al., *J Clin Invest*, Vol. 96, pp. 2924-2931 (1995); Cernadas et al., *Am J Respir Cell Mol Biol*, Vol. 20, pp. 1-8 (1999); and Williams and Galli, *J Exp Med*, Vol. 192, pp. 455-462 (2000).

The agents of the invention are also useful as co-therapeutic agents for use in combination with other drug substances, such as anti-inflammatory, bronchodilatory or antihistamine drug substances, particularly in the treatment of obstructive or inflammatory airways diseases, such as those mentioned hereinbefore, e.g., as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Such anti-inflammatory drugs include steroids, in particular, glucocorticosteroids, such as budesonide, beclamethasone dipropionate, fluticasone propionate, ciclesonide or mometasone furoate; or steroids, described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445 and WO 03/072592; non-steroidal glucocorticoid receptor agonists, such as those described in WO 00/00531, WO 02/10143, WO 03/082280, WO 03/082787, WO 03/104195 and WO 04/005229; LTB4 antagonists, such as those described in U.S. Pat. No. 5,451, 700; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene), SelCID™ CC-10004 (Celgene), KW-4490 (Kyowa Hakko Kogyo), WO 03/104204, WO 03/104205, WO 04/000814, WO 04/000839 and WO 04/005258 (Merck), as well as those described in WO 98/18796 and WO 03/39544; A2a agonists, such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462 and WO 03/086408; A2b antagonists, such as those described in WO 02/42298; and beta ($\beta$)-2-adrenoceptor agonists, such as albuterol (salbutamol), metaproterenol, terbutaline, salmeterol, fenoterol, procaterol, and especially, formoterol and pharmaceutically acceptable salts thereof, and compounds (in free or salt or solvate form) of formula (I) of WO 00/75114, which document is incorporated herein by reference, preferably compounds of the Examples thereof, especially a compound of formula

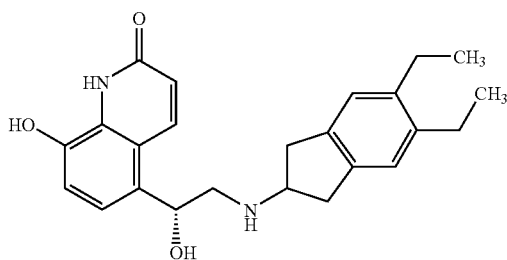 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula (I) of WO 04/16601. Further-β2-adrenoreceptor agonists include compounds, such as those described in WO 99/64035, WO 01/42193, WO 01/83462, WO 02/066422, WO 02/070490, WO 02/076933, WO 2004/011416 and US 2002/0055651.

Such bronchodilatory drugs include anticholinergic or antimuscarinic agents, in particular, ipratropium bromide, oxitropium bromide, tiotropium salts and CHF 4226 (Chiesi), but also those described in WO 01/04118, WO 02/51841, WO 02/53564, WO 03/00840, WO 03/87094, WO 04/05285, WO 02/00652, WO 03/33495, WO 03/53966, EP 0424021, U.S. Pat. Nos. 5,171,744 and 3,714,357.

Such co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and steroids, β-2 agonists, PDE4 inhibitors or LTD4 antagonists may be used, e.g., in the treatment of COPD or, particularly, asthma. Combinations of agents of the invention and anticholinergic or antimuscarinic agents, PDE4 inhibitors, dopamine receptor agonists or LTB4 antagonists may be used, e.g., in the treatment of asthma or, particularly, COPD.

Other useful combinations of agents of the invention with anti-inflammatory drugs are those with antagonists of chemokine receptors, e.g., CCR-1, CCR-2, CCR-3, CCR-4, CCR-5, CCR-6, CCR-7, CCR-8, CCR-9, CCR-10, CXCR1, CXCR2, CXCR3, CXCR4 and CXCR5; particularly useful are CCR-3 antagonists, such as those described in WO 2002/026723, especially 4-{3-[(S)-4-(3,4-dichlorobenzyl)-morpholin-2-ylmethyl]-ureidomethyl}-benzamide and those described in WO 2003/077907, WO 2003/007939 and WO 2002/102775.

Also especially useful are CCR-5 antagonists, such as Schering-Plough antagonists SC-351125, SCH-55700 and SCH-D; Takeda antagonists, such as N-[[4-[[[6,7-dihydro-2-(4-methyl phenyl)-5H-benzo-cyclohepten-8-yl]carbonyl]amino]phenyl]-methyl]tetrahydro-N,N-dimethyl-2H-pyran-4-aminium chloride (TAK-770); and CCR-5 antagonists, described in U.S. Pat. No. 6,166,037, WO 00/66558 and WO 00/66559.

The agents of the invention may be administered by any appropriate route, e.g., orally, e.g., in the form of a tablet or capsule; parenterally, e.g., intravenously; by inhalation, e.g., in the treatment of inflammatory or obstructive airways disease; intranasally, e.g., in the treatment of allergic rhinitis; topically to the skin, e.g., in the treatment of atopic dermatitis; or rectally, e.g., in the treatment of inflammatory bowel disease.

The present invention also provides a pharmaceutical composition comprising a compound of formula (I) in free form or in the form of a pharmaceutically acceptable salt, optionally together with a pharmaceutically acceptable diluent or carrier therefore. The composition may contain a co-therapeutic agent, such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight); and/or one or more surfactants, such as oleic acid or sorbitan trioleate; and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

The invention includes:
(a) an agent of the invention in inhalable form, e.g., in an aerosol or other atomizable composition or in inhalable particulate, e.g., micronised form;
(b) an inhalable medicament comprising an agent of the invention in inhalable form;
(c) a pharmaceutical product comprising such an agent of the invention in inhalable form in association with an inhalation device; and
(d) an inhalation device containing an agent of the invention in inhalable form.

Dosages of agents of the invention employed in practicing the present invention will of course vary depending, e.g., on the particular condition to be treated, the effect desired and the mode of administration. In general, suitable daily dosages for oral administration are of the order of 0.01-100 mg/kg. The invention is illustrated by the following Examples.

EXAMPLES

General Conditions

LCMS are recorded on an Agilent 1100 LC system with a Waters Xterra MS C18 4.6×100 5 μM column, eluting with 5-95% 10 mM aqueous ammonium bicarbonate in acetonitrile over 2.5 minutes, with negative ion electrospray ionization or 5-95% water+0.1% TFA in acetonitrile with positive ion electrospray ionization. [M+H]+ refers to monoisotopic molecular weights.

Abbreviations
DMF N,N-dimethylformamide
EtOAc ethyl acetate
Et$_2$O diethyl ether
HCl hydrochloric acid
MgSO$_4$ magnesium sulfate
NaH sodium hydride
NaOH sodium hydroxide
THF tetrahydrofuran
MeOH methanol
TFA trifluoroacetic acid The following examples have been prepared using the process described herein.

| Example | R | [M + H]+ |
|---|---|---|
| 1 | sulfonyl-morpholine | 430 |
| 2 | sulfonyl-pyrrolidine | 414 |
| 3 | sulfonyl-(4-methyl)piperazine | 443 |
| 4 | sulfonyl-piperidine | 428 |
| 5 | sulfonyl-azetidine | 400 |
| 6 | sulfonyl-N(methyl)(cyclohexyl) | 456 |

Example 1

Preparation of {2-methyl-1-[4-(morpholine-4-sulfonyl)-benzyl]-1H-pyrrolo[2,3-b]pyridine-3-yl}acetic acid a) 4(4-bromomethyl-benzenesulfonyl)-morpholine

To a stirring solution of commercially-available 4-bromomethyl benzenesulfonyl chloride (1.0 g, 3.71 mmol) in dichloromethane (8 ml) at 0° C. under an argon atmosphere, is added triethylamine (0.575 ml, 4.1 mmol), in one portion, followed by morpholine (0.359 ml, 4.1 mmol). The reaction mixture is stirred for 20 h, warming up slowly to room temperature. The reaction mixture is then diluted with 2N HCl aq (40 ml) and extracted with dichloromethane (20 ml), dried (MgSO$_4$) and evaporated to dryness in vacuo to afford the title compound. Used crude in next step.

b) {2-methyl-1-[4-morpholine-4-sulfonyl)-benzyl]-1H-pyrrolo[2,3-b]pyridin-3-yl}-acetic acid methyl ester NaH (46 mg, 1.14 mmol) as a 60% dispersion in mineral oil, is added to a solution of (2-methyl-1H-pyrrolo[2,3-b]pyridine-3-yl)-acetic acid methyl ester (212 mg, 1.04 mmol) in DMF (10 ml) at 0° C. under argon. After 1 h, 4(4-bromomethyl-benzenesulfonyl)-morpholine (400 mg, 1.25 mmol) is added, followed by sodium iodide (188 mg, 1.25 mmol). The reaction mixture is stirred allowing to warm up slowly to room temperature over 20 h. The reaction mixture is then poured into water (100 ml) and extracted with 1:1 EtOAc:Et$_2$O (40 ml), washed with brine and dried (MgSO$_4$). Evaporation to dryness in vacuo affords the crude product which is purified by column chromatography on silica gel eluting in 8:1 iso-hexane:EtOAc, increasing the polarity to 1:1 iso-hexane:EtOAc to elute the product. [M+H]$^+$ 444.

c) {2-methyl-1-[4-morpholine-4-sulfonyl)-benzyl]-1H-pyrrolo[2,3-b]pyridin-3-yl}-acetic acid To a stirring solution of {2-methyl-1-[4-morpholine-4-sulfonyl)-benzyl]-1H-pyrrolo[2,3-b]pyridin-3-yl}-acetic acid methyl ester (310 mg, 0.70 mmol) in 1:1 THF:MeOH (10 ml) at room temperature, is added 1 N NaOH aq (3 ml). The reaction mixture is left stirring over 20 h, then the reaction solvents are removed in vacuo, water (5 ml) is added and the product precipitated by treatment with 1 N HCl aq to pH 2-3. The title compound is collected by filtration and dried in vacuo. [M+H]$^+$ 430.

Example 2

Preparation of {2-methyl-1-[4-pyrrolidine-1-sulfonyl)-benzyl]-1H-pyrrolo[2,3-b]pyridin-3-yl}-acetic acid The title compound is prepared analogously to Example 1 by replacing morpholine with pyrrolidine to give {2-methyl-1-[4-pyrrolidine-1-sulfonyl)-benzyl]-1H-pyrrolo[2,3-b]pyridin-3-yl}-acetic acid. [M+H]+ 414.

Example 3

{2-methyl-1-[4-(4-methyl-piperazine-1-sulfonyl)-benzyl]-1H-pyrrolo[2,3-b]pyridin-3-yl}-acetic acid The title compound is prepared analogously to Example 1 by replacing morpholine with N-methylpiperazine to give {2-methyl-1-[4-N-methylpiperazine-4-sulfonyl)-benzyl]-1H-pyrrolo[2,3-b]pyridin-3-yl}-acetic acid. [M+H]+ 443

Example 4

{2-methyl-1-[4-piperidine-1-sulfonyl)-benzyl]-1H-pyrrolo[2,3-b]pyridin-3-yl}-acetic acid The title compound is prepared analogously to Example 1 by replacing morpholine with piperidine to give {2-methyl-1-[4-piperidine-4-sulfonyl)-benzyl]-1H-pyrrolo[2,3-b]pyridin-3-yl}-acetic acid. [M+H]+ 428.

Example 5

{1-[4-(Azetidine-1-sulfonyl)-benzyl]-2-methyl-1H-pyrrolo[2,3-b]pyridin-3-yl}-acetic acid The title compound is prepared analogously to Example 1 by replacing morpholine with azetidine to give {2-methyl-1-[4-azetidine-4-sulfonyl)-benzyl]-1H-pyrrolo[2,3-b]pyridin-3-yl}-acetic acid. [M+H]+ 400.

Example 6

{1-[4-(Cyclohexyl-methyl-sulfamoyl)-benzyl]-2-methyl-1H-pyrrolo[2,3-b]pyridin-3-yl}-acetic acid The title compound is prepared analogously to Example 1 by replacing morpholine with N-methylcyclohexylamine to give {1-[4-(Cyclohexyl-methyl-sulfamoyl)-benzyl]-2-methyl-1H-pyrrolo[2,3-b]pyridin-3-yl}-acetic acid. [M+H]+ 456.

The invention claimed is:
1. A compound of formula (I)

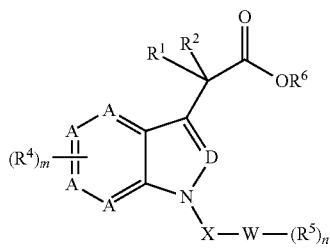

(I)

in free or salt form, wherein

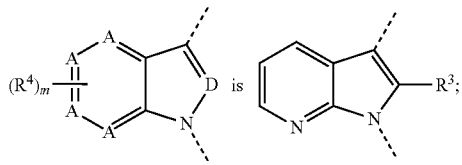

$R^1$ and $R^2$ are H;
$R^3$ is $C_1$-$C_8$-alkyl;
$R^5$ is

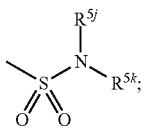

$R^{5j}$ and $R^{5k}$ are independently selected from H, and $C_1$-$C_8$-alkyl optionally substituted by a 4- to 14-membered heterocyclic group or $C_3$-$C_{15}$-carbocyclic group, or $R^{5j}$ and $R^{5k}$ together with the nitrogen atom to which they are attached form a 4- to 14-membered heterocyclic group;
$R^6$ is H or $C_1$-$C_8$-alkyl;
W is a $C_6$-$C_{15}$-aromatic carbocyclic group or a 4- to 14-membered heterocyclic group;
X is —$SO_2$—, —$CH_2$—, or —CON(Y)—;
Y is $C_1$-$C_8$ alkyl; and
n is 1.
2. A compound of formula (Ia)

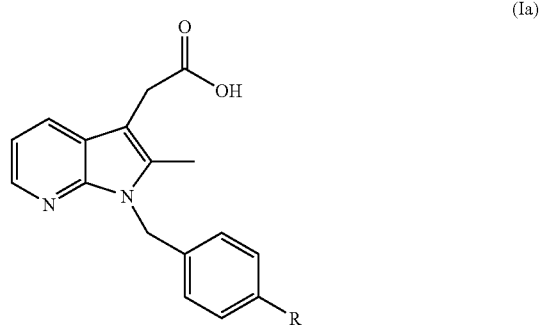

(Ia)

in free or salt form wherein
R is selected from the group consisting of

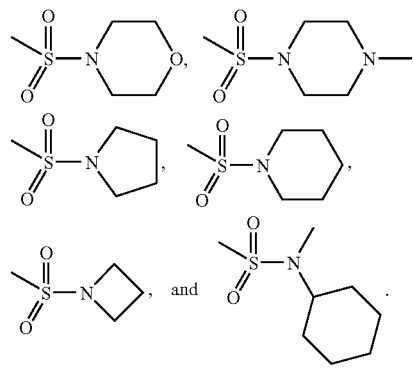

3. A compound according to claim 1 for use as a pharmaceutical.
4. A pharmaceutical composition, comprising:
the compound according to claim 1, and
a pharmaceutically acceptable diluent or carrier.
5. A pharmaceutical composition, comprising:
the compound according to claim 2, and
a pharmaceutically acceptable diluent or carrier.

* * * * *